United States Patent [19]

Small et al.

[11] Patent Number: 4,732,686
[45] Date of Patent: Mar. 22, 1988

[54] WEAK ELUANT ION CHROMATOGRAPHY

[75] Inventors: Hamish Small, Leland; Mark E. Soderquist; James W. Pischke, both of Midland, all of Mich.

[73] Assignee: The Dow Chemical Company, Midland, Mich.

[21] Appl. No.: 811,144

[22] Filed: Dec. 19, 1985

[51] Int. Cl.$^4$ .............................................. B01D 15/08
[52] U.S. Cl. ................................. 210/656; 210/198.2; 422/70; 436/150; 436/161
[58] Field of Search ......................... 210/635, 656–659, 210/198.2, 198.3, 673, 674; 422/70; 436/150, 161

[56] References Cited

U.S. PATENT DOCUMENTS

| | | | |
|---|---|---|---|
| 3,915,642 | 10/1975 | Small | 436/150 |
| 3,925,019 | 12/1975 | Small | 422/70 |
| 4,009,998 | 3/1977 | Benningfield | 436/150 |
| 4,039,442 | 8/1977 | Kadlec | 210/673 |
| 4,272,246 | 6/1981 | Fritz | 436/150 |
| 4,303,531 | 12/1981 | Kawabata | 210/673 |
| 4,455,233 | 6/1984 | Pohl | 422/70 |
| 4,556,463 | 12/1985 | Minz | 204/98 |

FOREIGN PATENT DOCUMENTS 56-144705  11/1981  Japan ................................. 210/674

Primary Examiner—Ernest G. Therkorn

[57]  ABSTRACT

Apparatus and method for the chromatographic separation and analysis of ionic species. This process is carried out utilizing, in an ion separator column, the combination of a low capacity, high performance resin as the stationary phase, and a weakly ionized electrolyte as the eluant or developing reagent, to effect resolution of ionic species in solution. For anion separation, a weak base resin of low capacity and high efficiency is used as the stationary phase, and a solution of a weak base or water as the mobile phase. For cation separation, a weak acid resin of low capacity and high efficiency is used as the stationary phase and a solution of a weak acid as the mobile phase. Because the eluant employed has a very low background conductivity, it will register only insignificantly on the readout from the conductivity cell. Thus, the method of the invention obviates the need for the eluant suppressor or "stripper" device used in conventional ion chromatography. The invention thereby enables continuous, uninterrupted measurements and eliminates the reservoirs, pumps, complex valving and electronics associated with such suppressor columns.

6 Claims, 9 Drawing Figures

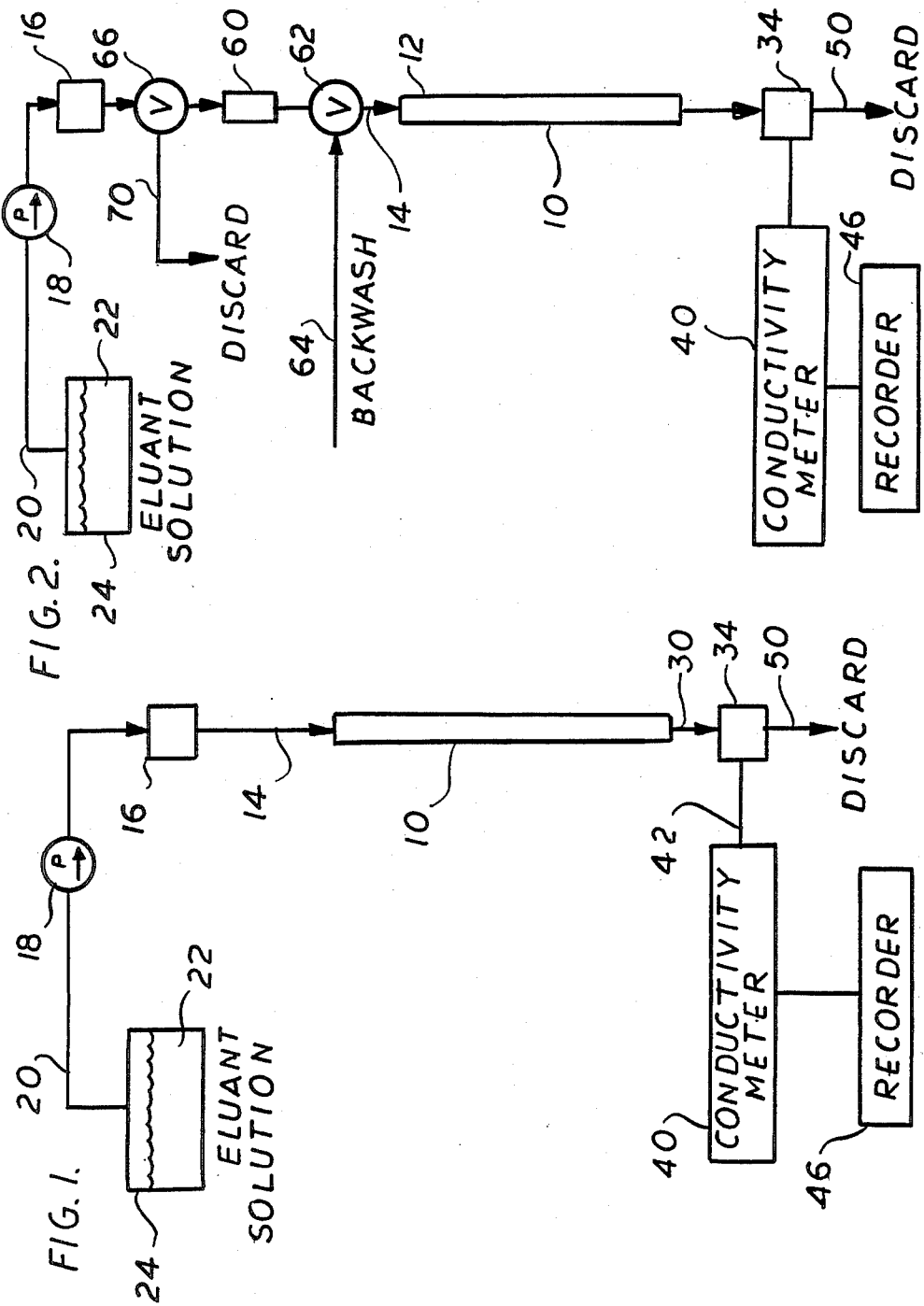

WEAK ELUANT ION CHROMATOGRAPHY

BACKGROUND OF THE INVENTION

The present invention relates to a method and to apparatus for chromatographic analysis of ionic species in solution. More particularly, the invention is directed to an improved method and apparatus by means of which chromatographic analysis may be conducted without the need for using a suppressor device to suppress the high background conductivity of eluants used in the analytical procedure.

Apparatus and methods for quantitatively analyzing ionic species utilizing liquid column chromatography are known in the art. Specific apparatus and techniques are described in H. Small et al., U.S. Pat. No. 3,920,397, issued Nov. 18, 1975, and T. S. Stevens et al., U.S. Pat. No. 4,474,664, issued Oct. 2, 1984 the entire disclosure of each of these patents is hereby specifically incorporated herein by reference, to the extent it is not inconsistent herewith.

The apparatus of the prior art has included the following distinct components as essential elements in the analytical method:
a. A chromatographic column.
b. An ion separator exchange resin supported in the column.
c. A suppressor device such as a column or hollow fiber device.
d. An eluant or developing agent, and
e. A detector and indicator such as a conductivity cell to monitor the effluent from the column and to identify the ionic species emanating therefrom.

The general procedure includes the steps of introducing into the column a solution containing the ions to be identified and analyzed. An eluant or developer solution is then added to the column to effect a spacial and time-correlated separation of the various ionic species as the latter traverse the resin bed. In order to prevent the eluant or developing reagent from interfering electrically with the detection of the ionic species to be analyzed, it has been the common practice to rely upon a second resin bed or hollow fiber suppressor to convert that reagent into weakly ionized (low conductivity products) without substantially interfering with the separation of the ionic species to be analyzed and passing through the column, or without significantly reducing their conductance.

Since its development, ion chromatography has proven to be a highly useful technique for the analysis of ions. A factor contributing to the usefulness of this technique is the capability of relying upon conductivity as a means for detecting the ions in the column effluent. The method itself has exhibited a broad universality, a high degree of sensitivity and speed, particularly in the analysis of inorganic ions. However, as heretofore practiced, despite the advantages indicated above, and others, the method itself suffers from several objectionable features. In some prior art procedures, objectionable features stem from the need to use a suppressor column for supressing the high background conductivity of the eluant or the developer, so that the sample ions may be detected without substantial interference.

In carrying out the types of analysis described, a prior art technique has been to employ a train of two columns, a separating column followed by a suppressor column. As indicated above, the first column operates to separate and resolve the ions by conventional elution chromatography. The prior art suppressor column functions to strip or to transform the eluant containing a highly conductive displacement ion to a less conductive level. This arrangement permits the ions of interest to be monitored by conductimetric detection. There are several drawbacks inherent in the technique described. A principal objection and inconvenience in many prior art metods is the need for frequent regeneration of the suppressor column, typically every eight to twenty four hours of operation. Other drawbacks are reduced resolution and sensitivity due to the band spreading in the suppressor column. Additionally, ion exclusion effects in the suppressor column can adversely affect ion separation. The suppressor column also results in increased back pressure and extended elution time. In some cases there are interfering or adverse reactions between the ions of interest and the materials contained in the second (the suppressor) column. Many of these objections have been obviated by the use of continuously regenerated membrane devices.

Because it is deemed more desirable to work with as simple a system as possible, there has been a continuing interest in developing a chromatographic analytical scheme which will operate effectively to separate ions without the need for a suppressor device, but which will still permit the use of conductimetric detection techniques.

It is an element of the present invention that there is provided an effective technique for utilizing a single column—the separator column—and no suppressor. While there has been some initial progress in this direction, for example, by applying conductimeric detection directly to the eluant from the ion exchange separator, the sensitivity of such prior art arrangements is compromised by the "noise" in the relatively high background conductivity of the eluant. It is, therefore, a principal aim of the present invention to provide a chromatographic analysis scheme which is effective to separate ions without the use of the suppressor column, and which effectuates the continued utilization of highly sensitive conductimetric detection as the means of ultimate analysis, as may be afforded when working in very low conductivity environments such as pure water.

SUMMARY OF THE INVENTION

It is an important feature of the invention that there is provided a chromatographic analysis scheme in which no suppressor device is needed, and which functions effectively to separate or to resolve ionic species which may then be detected and identified using conductimetric techniques.

It is a related feature of the invention that the method and apparatus are useful in the detection and analysis of both anions and cations.

It is yet another feature of the invention that the use of suppressor devices has been eliminated, greatly simplifying the overall components and operation of the ion chromatography device.

A related feature of the invention is that it simplifies and renders feasible the making of continuous, uninterrupted measurements.

A related feature of the mode of operation of the present invention is that it is highly advantageous in process control instruments and especially in remotely positioned monitoring devices.

Yet another important feature of the present invention is that it provides enhanced freedom to use a variety of eluants, including water, not generally suitable for use with methods employing suppressor columns.

It will be appreciated that the method of the invention provides improved efficiency since it renders possible the delivery of the effluent from the analysis column directly into the detector.

It is a feature of the method and apparatus of the invention that the conductance of the eluant used is sufficiently low so that the use of a suppressor device may be eliminated and the separated ions may be detected using simple conductance measuring devices.

A related feature of the invention is that the ion exchange resin used in the resin bed of the column has a very low exchange capacity but is characterized by high efficiency.

It will be appreciated that because of the low exchange capacity of the resins employed, only very dilute solutions of the active eluants are needed.

As adapted for the analysis of anions, the method of the invention utilizes a column in which the resin bed or stationary phase of the chromatographic column constitutes a weak base resin of very low capacity and the eluant solution or mobile phase also constitutes either a weak base or simply pure water.

In the analysis of cations according to the method and apparatus of the invention, the stationary phase or resin bed of the column constitutes a weak acid resin of very low capacity, and the eluant solution or mobile phase of the system is also a weak acid. Preferably, the eluant solution is an aqueous solution.

The anions to be analyzed are conveniently injected as their acids and migrate down the column, partitioning between the mobile base and the stationary weak base resin. As the anions emerge from the column as salts, or acids they may be detected and quantified by conventional conductance cells, meters, or recorders or such apparatus in combination. As an alternative procedure the anions may be injected as their salts, under which conditions a small pre-column is used to convert the anion to its acid. Because the pre-column is depleted only by the counter ions from the sample and not by the eluant, the need to regenerate this column is virtually eliminated.

The cations to be analyzed are injected as their bases and migrate down the column, partitioning between the mobile acid and the stationary weak acid resin. Again, the cations emerge as their salts and are conveniently detected in the established and well-known manner.

An important advantage of the present technique over prior art procedures is a markedly improved and greater sensitivity for weak electrolytes.

Other and further objects, features, and advantages of the invention will be evident from a reading of the following description considered in conjunction with the drawing.

BRIEF DESCRIPTION OF THE DRAWINGS

FIG. 1 is a schematic representation of the component elements of a chromatographic analytical system of the type finding utility in the practice of the present invention and showing the eluant supply solution, a stage for introduction of the sample to be analyzed, the separating column, and the conductivity sensing and data recording apparatus;

FIG. 2 is a schematic representation similar to that shown in FIG. 1 but including, in addition, a "pre-column" for treating samples introduced in their salt form and converting these samples into forms suitable for separation in the separating column;

DETAILED DESCRIPTION OF PREFERRED EMBODIMENTS

Figure 3:
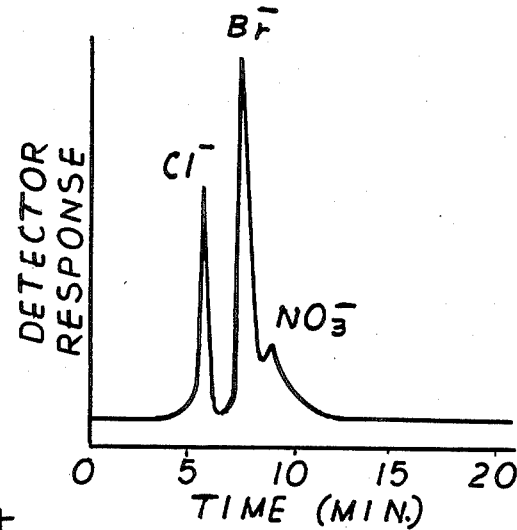
FIG. 3 is a chromatogram illustrating schematically the time-spaced resolution of the ionic species chloride, bromide and nitrate using weak base agglomerated resin in accordance with the method of the invention.

The aims and objects of the invention are achieved, and the chromatographic separation and analysis of ionic species are carried out by using, in an ion separator column, the combination of a low capacity, high performance resin as the stationary phase, and a weakly ionized electrolyte or water as the eluant or developing reagent. The system described enables one to dispense with the use of a suppressor device for the suppression of ionic species contained in the eluant, such species ordinarily interfering with the desired detection of those ions being resolved in the chromatographic column. For anion separation the combination of a weak base resin of low capacity and high efficiency is used as the stationary phase, while a solution of a weak base or water is used as the mobile phase. For cation separation, the combination used is a weak acid resin of low capacity and high efficiency as the stationary phase, and a solution of a weak acid as the mobile phase. Since the eluant or resolving solution employed has a very low background conductivity, it will register only insignificantly on the read-out from the conductivity cell. Hence, the method of the invention obviates the need for suppressor columns or stripper beds as used in conventional ion chromatography.

Avoidance of the need for and the use of a suppressor device eliminates many of the drawbacks associated with such devices. Regeneration is no longer a necessary procedure, band spreading is reduced, ion exclusion effects are minimized, back pressure and elution time are reduced, and sensitivity to weak electrolytes is enhanced.

While the general laboratory analytical techniques for preparing and charging separation columns and for carrying out the procedures in chromatographic analysis are know and described in the literature, the following brief specific descriptions are provided for purposes of convenient reference and as illustrative of the procedures by which the improved methods of the present invention are conducted.

Referring first to the drawings, the apparatus of the present invention is indicated schematically in FIG. 1 as consisting of chromatographic separation column 10 connected at its input end 12 through a conduit 14 to a sample injection valve 16, the sample itself being introduced in any preferred manner but preferably by means of a syringe (not shown) coupled through the injection valve 16. A pump 18 in a delivery line 20 feeds eluant solution 22 from a reservoir 24, and the analytical sample introduced into the injection valve 16 is thereby delivered to the separation column 10. Resolution of the ionic species takes place in the column 10 and the solution from the column, containing the ionic species, passes from column 10 through a delivery conduit 30 to a conductivity cell 34. Fluctuations in the conductivity which occur in the cell 34 are sensed by a conductivity meter 40 connected 42 electrically to the cell 34, and a recording device 46 provides a visible signal which is plotted as a chromatogram (FIGS. 3 through 9). The conductivity meter 40 in conjunction with the recorder 46 constitute read-out means for the signal fluctuations which occur in the conductivity cell 34. Sensed and spent eluant is discarded 50 from the conductivity cell 34, as indicated schematically in FIG. 1.

A second preferred embodiment of the apparatus used in the practice of the present invention is shown in FIG. 2. The structure and the relative arrangement of component elements there depicted correspond essentially to what is shown in FIG. 1, with the exception that there is provided a pre-column 60 and an associated back wash valve 62 and supply line 64 as well as a discard valve 66 and conduit 70, all interposed between the injection valve 16 and the entry port 12 to the column 10. The "pre-column" is used when one wishes to analyze salts. Specifically, the pre-column converts anions to the acid, and cations to the base. Since the pre-column 60 is depleted only by the "salt" of the sample, and not by the eluant, the column 60 has a very long life.

Neither the diameter (inside) of the columns used, nor the length of the columns is critical in the practice of the present invention. Nor is the size of the sample or the rate of throughput. For purposes of disclosure and not in any limiting sense there is provided herebelow a detailed description of the preparation and packing of a typical separation column for the analysis of cations and for the analysis of anions.

For the cations, a weak acid resin of very low capacity is used as the stationary phase and a solution of a weak acid as the mobile phase. For anions, a weak base resin of very low capacity is used as the stationary phase and a solution of a weak base as a mobile phase.

EXAMPLE 1

Preparation of Cation Column

A weak (carboxylic) acid resin (Dowex ® CCR-2) was thoroughly ground in a ball mill and the larger particles, for example, those greater than 1 micron, and the fines were removed by centrifugal sedimentation. An approximately 0.5% suspension of the selected particles was then pumped through a 3×250 mm. glass column packed with the $HCO_3^-$ form of the resin (Dowex ® 1×8) at a flow rate of about 8 ml./hr. When the suspension was observed in the effluent, the column was flushed with water. The thus established substrate or resin bed had a particle size of 38 plus or minus 4 micron and was prepared by elutriation of 200/400 mesh Dowex ® 1×8.

EXAMPLE 2

Preparation of Anion Column

A 9 mm. (inside diameter) glass column was gravity packed with 36±4 micron pyridine base resin (Dowex ® 50 in the pyridine H+ form) from a dilute slurry in water. After standing overnight the resulting bed was found to be 146 mm. deep. After testing, the column was agglomerated by pumping a very dilute suspension of a fine grind of Dowex ® WGR through the column. A short filter column packed with 20 micron Dowex ® 50W×8 was used to prevent any oversized particles from reaching the column. When the suspension was observed in the effluent, the column was flushed with water.

The eluant used for conducting the anion analysis was 0.05 N pyridine. For cation analysis, the eluant was 0.01 N $H_2CO_3$ except as otherwise noted. The latter was generated by passing 0.01 N $NaHCO_3$ through a large bed of the hydrogen form of Dowex ® 50W×8 resin. All eluants were made up from double-distilled de-ionized water and were filtered through 1.2 micron Millipore filters.

EXAMPLE 3

Use of Pre-column

Since anions can be separated by weak base eluants only when they are injected in their acid form (HCl, HBr, $H_2SO_4$), a method was devised for analyzing ionic species in their salt forms (NaCl, KCl, and $CaCl_2$). Conveniently, the problem has been solved, in accordance with practice of the invention, by introducing a pre-column between the injection valve 16 and the separating column 10 (FIG. 2) so as to convert the anions directly to the pyridine salt, and cations to their corresponding eluant salts, for example, sodium chloride to sodium bicarbonate. Specifically, a small (3×100 mm.) column of 200/400 mesh Dowex ® 50W×8 (pyridine form resin) was placed between the injection valve 66 and the weak base analytical column 10. In this particular procedure the separating column was a 3×250 mm. glass column packed with 200/400 mesh surface-sulfonated S/DVB copolymer onto which a finely ground suspension of Dowex WGR weak base resin was agglomerated.

With the pre-column 60 in place it was found that the elution times (tr) for all salts of a particular anion had the same elution time as did the acid form. When the pre-column was removed, however, the elution time was also found to be the same for the salt and for the acid forms. After several sample injections it was noted that the elution time was becoming shorter. Continued injections of samples caused further reduction in the elution time until, finally, all samples eluted at the void volume time (to). The conclusion drawn was that surface sulfonated support resin acted to convert the salts, just as did the pre-column. However, because of the low total capacity of the resin, the latter was exhausted after only a few tens of samples. Accordingly, the pre-columns serves a most useful role, particularly since the life of the pre-column itself is determined by the amount of "salt" in the sample, and not by the eluant. It may be calculated that when using a 3×100 mm. pre-column packed with Dowex ® 50W×8 of capacity in the order of 2.0 meq/cm.$^3$, a sample loop of 0.02 cm.$^3$, and an average concentration of 0.01 meq/cm.$^3$, the pre-column could be used for longer than one year without exhaustion, even at the rate of 20 minutes per sample, eight hours per day, five days per week.

Moreover, when attached to a 3×500 mm. analytical column, the effect of the pre-column on resolution is essentially negligible, while pressure and elution time are only slightly increased. The pre-column serves also as a guard column, protecting the analytical column from "dirty" samples which might plug it.

The pre-column may be eliminated altogether by using fully functional support (Dowex® 50W×8) rather than surface sulfonated copolymer. Under such conditions there will result a gradual reduction in the elution time (tr) with use. Under such conditions, the column may be regenerated about every week or so to prevent significant variations in the elution time.

EXAMPLE 4

Substantial improvements in column efficiency were achieved for anion columns by using small, nearly monodispersed (36±4μ) Dowex® 50W×8 as a support rather than the coarser 200/400 mesh surface sulfonated copolymer. Still further improvement was obtained by packing in a relatively wide (9 mm) column. Before agglomeration such columns were found to have an HETP (height equivalent to a theoretical plate) of about 0.05 mm. After agglomeration with a fine suspension of weak base resin, a substantial increase in HETP resulted.

Despite any loss of efficiency experienced through the mode of packing and the types of packing used, the efficiency of columns used in accordance with the method of the present invention is markedly greater than those heretofore realized. Complete base line separation of $Cl^-$ and $Br^-$ was achieved in only 15 cm. and $Br^-$ and $NO_3^-$ were also partially resolved (FIG. 3). A 50 cm. column would thus provide substantially complete resolution of the $Br^-$ and the $NO_3^-$.

EXAMPLE 5

Figure 4:
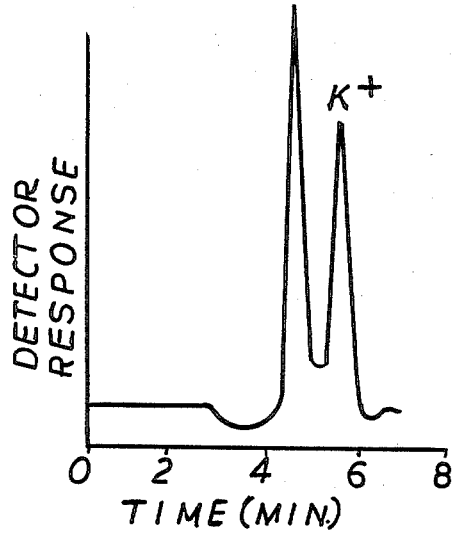
FIG. 4 is a chromatogram similar to FIG. 3 but pertaining to the ionic species sodium ion and potassium ion.

Using uniform (38±4μ) Dowex 1×8 ($HCO_3^-$ form) as a support, and agglomerating with a fine grind of a carboxylic acid resin (Dowex® CCR-2), a column was produced exhibiting good efficiency and selectivity. As illustrated in FIG. 4, using $H_2CO_3$ as the eluant, it was possible to obtain nearly baseline resolution.

EXAMPLE 6

Figure 5:
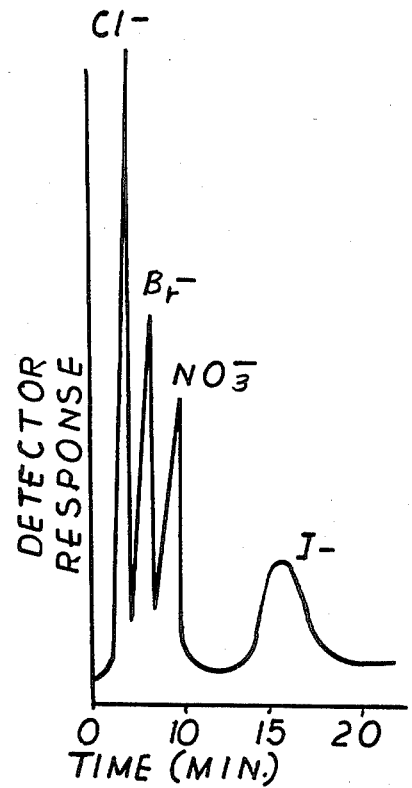
FIG. 5 is a chromatogram showing the resolution of the ions chloride, bromide, nitrate and iodide.
Figure 6:
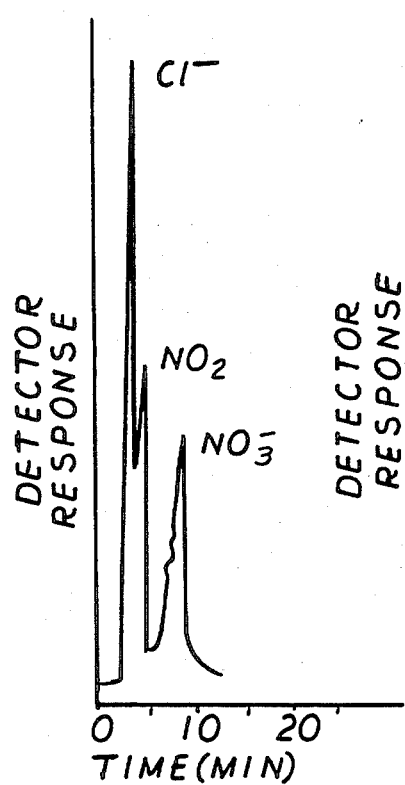
FIG. 6 is a chromatogram similar to FIG. 5, but showing the resolution of the ions chloride, nitrite and nitrate.
Figure 7:
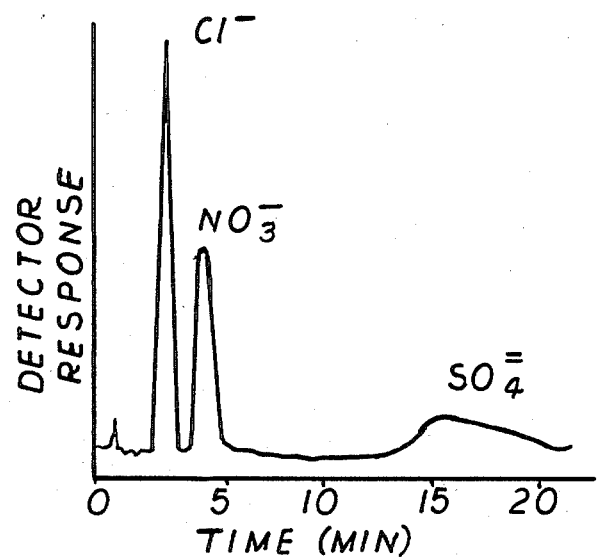
FIG. 7 shows the resolution of chloride, nitrate and sulfate using pyridine as the eluant.

A further example of the separation of anion mixtures using weak base agglomerated resin (ground poly (4-vinyl pyridine deposited on Dowex® 50-8X resin) is illustrated in FIG. 5 for $Cl^-$, $Br^-$, $I^-$ and $NO_3^-$ and in FIG. 6 for $Cl^-$, $NO_3^-$ and $NO^-_2$. In these separations, water was used as the eluant.

It is within the inventive concept and contemplation of the present invention that chromatographic analysis be carried out utilizing a weak base resin of low capacity and high efficiency and water as the eluant. While in certain systems this has proved feasible, in others the basicity of the weak base resin was found to be too high to permit the desorption step of the anions to take place with the desired ease. (The addition of pyridine to the eluant provided sufficient displacement strength to elute the anions from the column. Pyridine being poorly dissociated exhibits relatively low conductivity and thus does not interfere with the conductimetric analysis of the ionic species being detected and quantified.)

EXAMPLE 7

The method of the invention was used to resolve the anions of strong acids. The anions, for example, $Cl^-$, $NO_3^-$ and $SO_4^=$ when injected as their acids, migrated down the column, partitioning between the mobile base and the stationary phase.

The mobile pyridine eluant, coupled with the acid form of the ionic species traversed the weak base resin and the anions emerged from the column as the highly dissociated salt of the weak base. Upon detection, a chromatogram was obtained (FIG. 7) which illustrates the separation of HCl, $HNO_3$ and $H_2SO_4$ using weak base agglomerated resin (agglomerated Dowex® 44 to surface-sulfonated vinyl benzene copolymer), and the elutriant being 0.08 M pyridine.

EXAMPLE 8

Use of Water as the Eluant

A detailed example of the use of an agglomerated weak base resin in accordance with the principles of the invention is set forth below:

Poly(4-vinyl pyridine-co-divinylbenzene), 2% cross-linked, was thoroughly ground using a ball mill. Fine particles were separated by slurrying the ground polymer with water, allowing the heavier particles to settle, then draining off substantially all of the water fraction. This process was repeated three times. Five grams of the ground polymer from the second settling was added to the 25 ml of fresh deionized water. The grindings were sonicated, i.e., exposed to high frequency sound waves, for ten minutes in order to break down any particle agglomeration. Four grams of Dowex® 50-8X, (in $H^+$ form, 37-44 cation exchange resin) was added to the above solution of ground polymer and the mixture was vigorously shaken for 10 minutes. Additional mixing followed for 30 minutes, using a circular rotating wheel. The agglomerated resin was then allowed to settle for 10 minutes. The supernatant was decanted off and discarded. Final washings were done with three separate additions of 100 ml of deionized water. A suspension of the agglomerated resin was injected into the column, using a 10 ml disposable plastic syringe.

In initial developmental work a cation exchange resin (Dowex® 50-8X) coated with a low molecular weight weak base polymer poly(4-vinyl pyridine) in the ratio of two exchange sites of the resin with two pyridine moieties of the linear polymer chain. It was found that increased resin capacity was desirable in order to achieve optimum separation.

Accordingly, surface-sulfonated sytragel beads were coated with the weak base pyridine polymer. Compared with the Dowex® 50-8X cation exchange resin referred to above, the sulfur sulfonated beads have fewer binding sites available for the pyridine polymer. Nevertheless, it was found that still further increase in resin capacity would be advantageous.

The capacity of the supporting resin bed was then further increased by agglomerating a cross-linked polymer to a resin. The resulting structure leaves a greater number of binding sites exposed to the solution as compared with the earlier polymer coatings produced. Several common anions were then injected as their acids. The results, which are listed in Table I suggested that a number of separations were possible using the agglomerated weak base resin and water as the eluant. This proved to be the case, typical separations at 22 degrees C. being shown in FIGS. 5 and 6.

TABLE I

Elution of Anions by Water
Separating Column: 2.8 mm × 300 mm
"Agglomerated Poly(4-VP-DVB) to Dowex ® 50-8X"

| Anion Injected (0.001 M) | Elution Time (min) at 25° C. |
|---|---|
| HCl | 3.30 |
| HBr | 5.45 |
| $HNO_2$ | 4.20 |
| $HNO_3$ | 8.66 |
| $H_2SO_4$ | 5.73 |
| KI | 21.60 |

EXAMPLE 9

Figure 8:
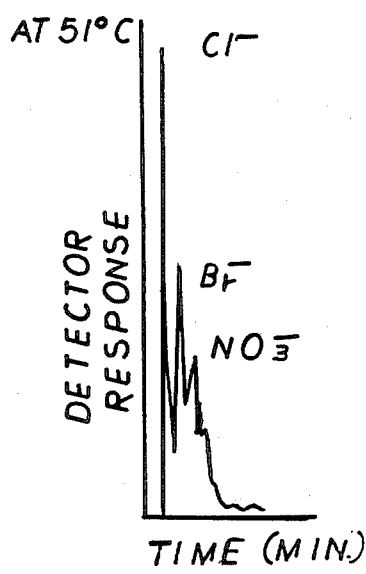
FIGS. 8 and 9 are chromatograms illustrating the effect of temperature on the separation of chloride, bromide and nitrate, water being used as the eluant.
Figure 9:
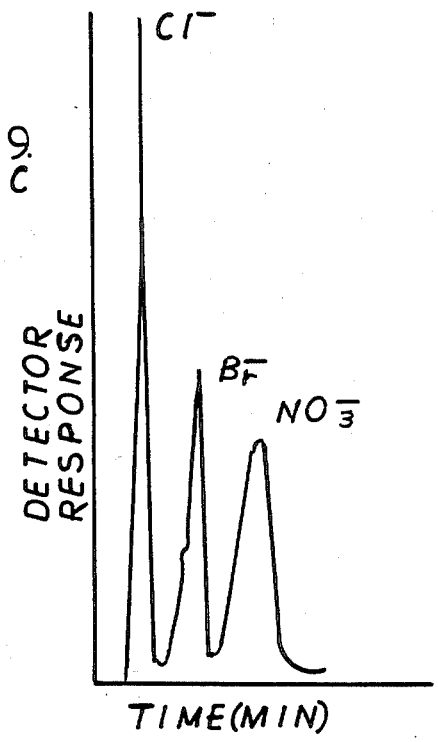

Relying on the principle that increase in temperature tends to increase the degree of dissociation of weak electrolytes, the resolution of the described system, using water as the eluant, was enhanced and good base line resolution of $Cl^-$, $Br^-$ and $NO_3^-$ was achieved by cooling to 4° C. as compared with resolution at 51° C., as shown in FIGS. 8 and 9.

The term "high performance" as used herein is intended to indicate that the ionic species involved are cleanly and sharply separated so that the read-out apparatus provides sharp concentration peaks and good baseline separation between substantially all of the peaks involved. The system described is one in which the ionic species do not penetrate deeply into the resin structure and are not otherwise held up during development of the chromatographic separation. In preferred embodiments of the invention the separator resin is pellicular, having its active sites at or near the surface of the resin beads.

In preferred procedures of the invention the resins used also exhibit relatively low specific capacity so that only relatively small quantities of developing agent are required to effect the separation and elution of the ionic species from the resin bed.

In carrying out the analysis of ionic species, in accordance with and using the apparatus of the present invention, sample preparation techniques and introduction of the sample into the separator column are achieved in accordance with well-established procedures and techniques using commercially available apparatus such as sample injection valves, all as well understood in the art.

While preferred detailed procedures and apparatus have been described and specific examples have been provided, it will be understood by those skilled in the art that many variations and modifications may be made within the scope of the present invention, without the exercise of the inventive faculty. All such changes and modifications are considered to be part of the present invention, the invention being limited only by the appended claims.

What is claimed is:

1. A method for eliminating the need for an eluant suppressor device in the chromatographic separation and detection of ionic species present in solution, each of the species being of the same valence sign,
   said method comprising:
   supporting in a column for ion separation, a resin bed including chromatographic resin comprising a low capacity, high-performance stationary phase for controlled interaction with ionic species to be introduced into the column,
   introducing into the column a solution containing ionic species to be separated and analyzed,
   introducing into the column a solution of developing reagent of weakly ionized electrolytes selected from the group consisting of water, pyridine, $H_2CO_3$, and mixtures thereof for eluting ionic species present in the column,
   regulating solution flow through the column and passing the solution containing the ionic species and the solution of the developing reagent through the column and through the resin contained therein,
   eluting the ionic species with the solution and effecting a resolution of and chromatographic separation of the ionic species as the species traverse a flow path through the column,
   sensing and detecting ionic species passing through the resin bed and delivered from the column,
   providing visually perceptable indicia correlated with specific ionic species emanating with an effluent solution discharged from the column, and
   identifying ionic species in the effluent solution discharged from the column.

2. The method as set forth in claim 1 wherein said solution of developing reagent means is water.

3. In the method of chromatographic analysis of a plurality of species of ions in sample solutions and including the steps of
   introducing into a separator column A a sample solution containing ionic species of interest, containing a resin bed including an ion exchange resin,
   adding a developing solution to the sample-containing separator column to resolve ionic species present in the sample solution and to elute the ionic species from the resin bed of the column separator for conductivly detecting the separated ionic species carried through the resin and delivered from the separator column, and for producing visually perceptible indicia of the ionic species,
   the improvement wherein the resin in the resin bed comprises a low capacity, high-performance stationary phase retained in the separator column, and
   wherein the developing solution for eluting the ionic species of the sample solution comprises a solution of a weakly ionized electrolytes selected from the group consisting of water, pyridine, $H_2CO_3$, and mixtures thereof, said improvement being characterized in effectively obviating the need for an eluant suppressor column of the type conventionally used for substituting ions of lesser conductivity for highly conductive ions which are ordinarily contained in the eluant and which interfer with conductive detection of ions of interest.

4. The improvement as set forth in claim 3 wherein the ionic species are anions, the resin is a weak base resin, and the eluant is a dilute aqueous solution of pyridine.

5. The improvement as set forth in claim 3 wherein the ionic species are cations, the resin is a weak acid resin, and the eluant is a dilute solution of $H_2CO_3$.

6. The improvement as set forth in claim 3 wherein said developing solution is water.

* * * * *

UNITED STATES PATENT AND TRADEMARK OFFICE
CERTIFICATE OF CORRECTION

PATENT NO. : 4,732,686

DATED : March 22, 1988

INVENTOR(S) : Hamish Small; Mark E. Soderquist; James W. Pischke

It is certified that error appears in the above-identified patent and that said Letters Patent is hereby corrected as shown below:

Col. 1, line 59, after "features" insert -- which interfere with the wide acceptance and the general utility of the method itself --;

line 61, "supressing" should read -- suppressing --.

Col. 2, line 8, "metods" should read -- methods --.

Col. 3, line 37, "alternative" should read -- alternate --.

Col. 4, line 57, "know" should read -- known --.

Col. 5, line 54, "$HCO-_3$" should read -- $HCO_3^-$ --.

Col. 6, line 38, insert -- ® -- after "Dowex";

lines 53-54, "pre-columns" should read -- pre-column --.

Col. 7, line 34, "$HCO-_3$" should read -- $HCO_3^-$ --;

line 66, "$SO_4=$" should read -- $SO_4^-$ --.

Col. 9, line 17, "dissociation" should read -- disassociation --.

Col. 10, line 21 (in Claim 1), "perceptable" should read -- perceptible --;

line 27 (in Claim 2), delete "means";

line 38 (in Claim 3), "conductivly" should read -- conductively --.

Signed and Sealed this

Third Day of October, 1989

Attest:

DONALD J. QUIGG

Attesting Officer

Commissioner of Patents and Trademarks